(12) United States Patent
Schneider et al.

(10) Patent No.: US 8,545,542 B2
(45) Date of Patent: Oct. 1, 2013

(54) TANNING DEVICE AND METHOD THEREFOR

(75) Inventors: Denise Schneider, Wadell, AZ (US); Brian Bautista, Tempe, AZ (US)

(73) Assignee: Shoulder Rayz, LLC, Flagstaff, AZ (US)

( * ) Notice: Subject to any disclaimer, the term of this patent is extended or adjusted under 35 U.S.C. 154(b) by 0 days.

(21) Appl. No.: 13/217,087

(22) Filed: Aug. 24, 2011

(65) Prior Publication Data

US 2013/0053930 A1 Feb. 28, 2013

(51) Int. Cl.
*A61N 5/06* (2006.01)

(52) U.S. Cl.
USPC .............................................. 607/88; 607/89

(58) Field of Classification Search
USPC ...................................................... 607/88–95
See application file for complete search history.

(56) References Cited

U.S. PATENT DOCUMENTS

| | | | | |
|---|---|---|---|---|
| 4,600,009 A * | 7/1986 | Kramer et al. | | 607/91 |
| 4,856,087 A * | 8/1989 | Nesbit | | 455/344 |
| 4,964,183 A * | 10/1990 | LaForce, Jr. | | 5/421 |
| 6,773,319 B1 * | 8/2004 | Carlini, Jr. | | 441/130 |
| 6,802,854 B1 * | 10/2004 | McFarland | | 607/91 |
| 2004/0167591 A1 * | 8/2004 | Brown, Jr. | | 607/95 |

* cited by examiner

*Primary Examiner* — Bill Thomson
*Assistant Examiner* — Jeffrey Lipitz
(74) *Attorney, Agent, or Firm* — Weiss & Moy, P.C.; Jeffrey D. Moy

(57) ABSTRACT

A tanning device has one or more reflective surface areas. The reflective surface areas may be used for redirecting light rays toward one or more parts of a user's body. A pair of speakers are positioned in the tanning device.

6 Claims, 3 Drawing Sheets

TANNING DEVICE AND METHOD THEREFOR

RELATED APPLICATIONS

The present application claims the benefit to and is related herewith to U.S. patent application entitled, "Tanning Device and Method Therefor", filed Jul. 14, 2009, and having U.S. Ser. No. 61/225,459, in the name of Denise Schlecht, now Denise M. Schneider, and Brian Bautista, and which is incorporated herein by reference in its entirety.

FIELD OF THE INVENTION

This invention relates to tanning, and more specifically, to a tanning device that redirects light rays toward one or more parts of the body of the user.

BACKGROUND OF THE INVENTION

Sun tanning is an activity practiced by many. In order to allow for year-round tanning, beauty salons and indoor tanning establishments commonly use a device known as a tanning bed. The tanning bed is typically a coffin-like enclosure that has tanning light bulbs running the length of the bed on the interior of the bed, both above, below, and to the sides of the area where the user of the tanning bed is positioned. However, due to the orientation of the light bulbs within the tanning bed, the tanning bed oftentimes fails to cause light to be directed toward the upper shoulders of the user. Tanning beds are sometimes retrofitted to cure this defect by placing a horizontal reflective surface at the end of the tanning bed near the user's head, but this modification can be costly.

Therefore, a need existed to provide a device and method to overcome the above problem. The device and method redirect light rays to different areas of a user's body.

SUMMARY OF THE INVENTION

In accordance with one embodiment, a light reflector for tanning is disclosed. The light reflector has a main section for resting a desired portion of a body of a user. Side members are attached to the main section. A reflective coating is formed on the side members to reflect light to a desired location on the body of the user. A pair of speakers are positioned in the side members.

BRIEF DESCRIPTION OF THE DRAWINGS

Common reference numerals are used throughout the drawings and detailed description to indicate like elements.

DETAILED DESCRIPTION

Figure 1:
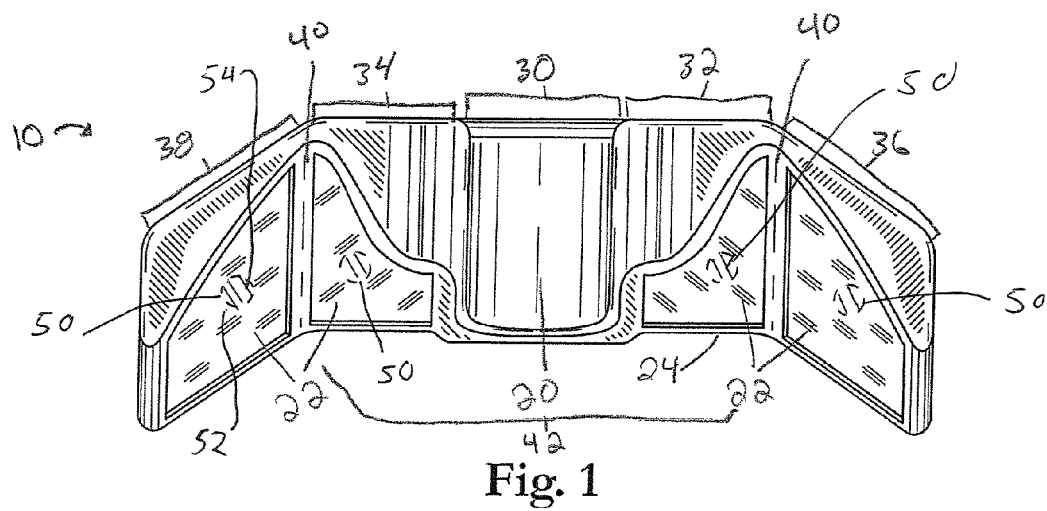
FIG. 1 is a top perspective view of one embodiment of the present invention.
Figure 2:
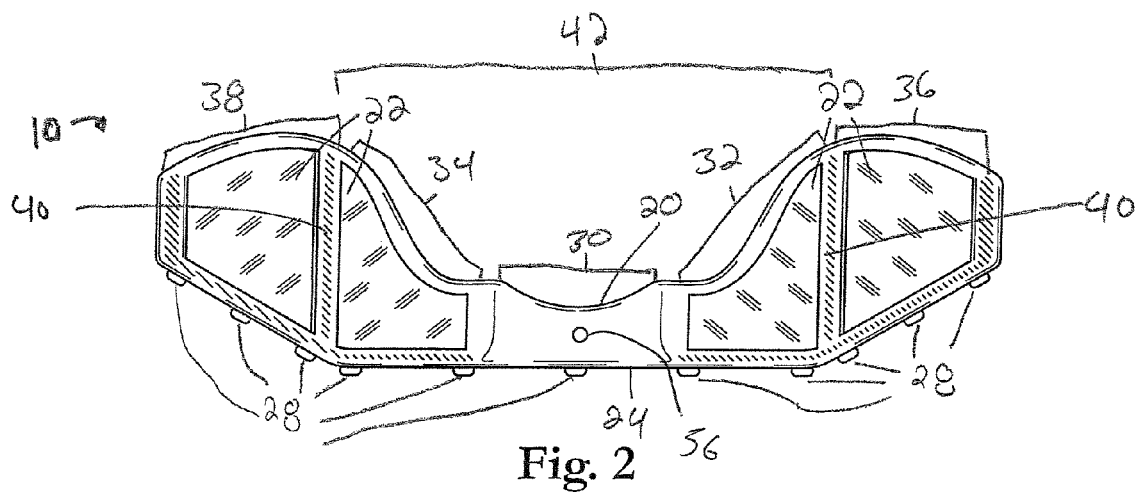
FIG. 2 is a bottom perspective view of the embodiment of FIG. 1.
Figure 3:
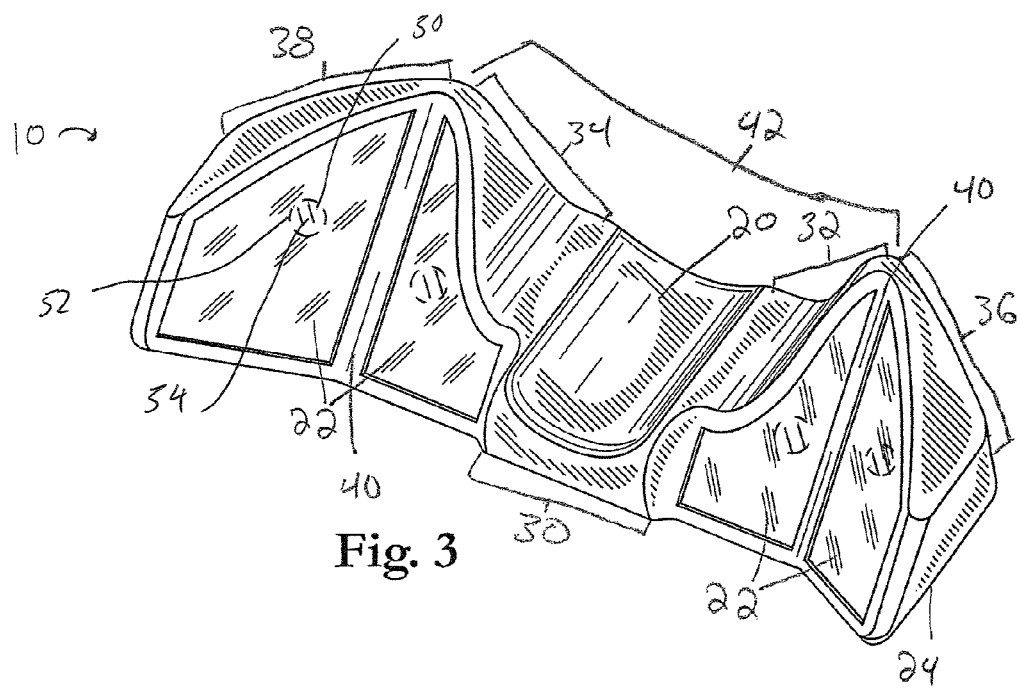
FIG. 3 is a second top perspective view of the embodiment of FIG. 1.
Figure 4:
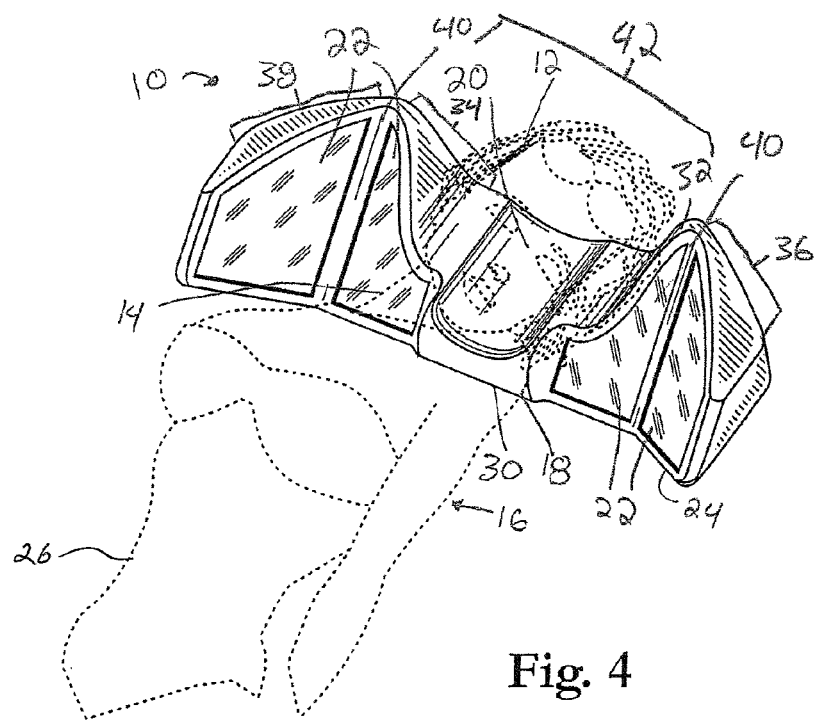
FIG. 4 is the top perspective view of FIG. 3 with a user using the device, the user shown in phantom.
Figure 5:
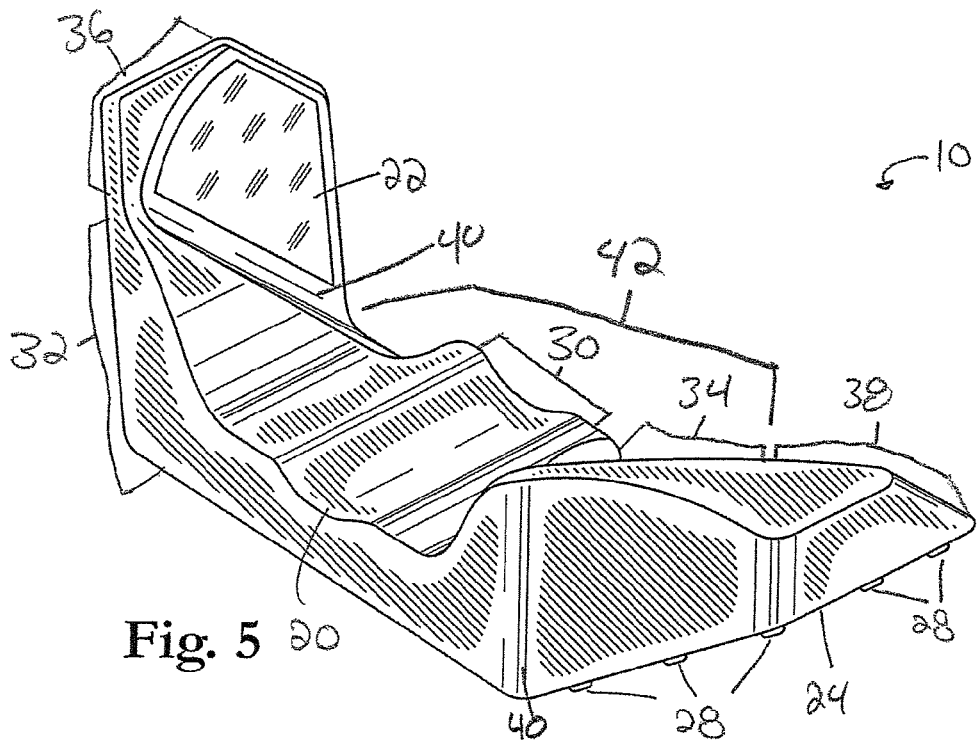
FIG. 5 is a perspective view of the embodiment of FIG. 1 showing a portion of the rear of the device.
Figure 6:
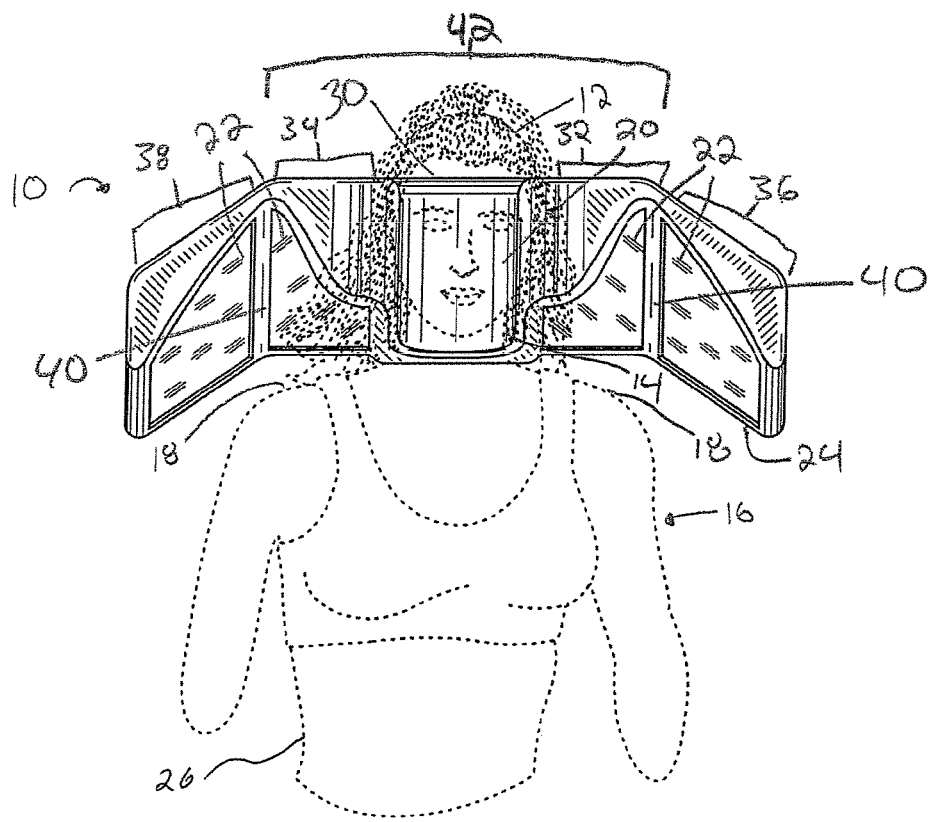
FIG. 6 the top perspective view of FIG. 1 with a user using the device, the user shown in phantom.

One way to effectively ensure that a sunbather or tanning bed user receives light rays on their body is to provide a reflective device that redirects the ambient light or the light produced by the tanning bed toward their body. Referring to FIGS. 1-6, one embodiment of a tanning device 10 is shown. The tanning device 10 may redirect rays of light to different areas of a body 26 of a user 16 (shown in FIGS. 4 and 6). In the present embodiment, the device 10 may be used to redirect light rays emitted by a tanning bed. However, the device 10 may also be used to redirect sunlight while tanning outdoors.

The tanning device 10 has a main body 42. In the present embodiment, the main body 42 may be formed from a single foam injection mold. However, an alternative embodiment of the tanning device 10 may have a main body 42 having different sections formed individually, or the tanning device 10 may be made of a different material or via a different method. The tanning device 10 may also have two outer wing members 36 and 38 which form angles 40 with the main body 42. In accordance with one embodiment, these angles 40 may be made adjustable. The angles 40 may be made adjustable by having a bendable wire disposed within the tanning device 10 or by the wing members 36 and being made from their own individual molds and then coupled to the rest of the tanning device 10 by hinges, VELCRO, or other coupling means. Such adjustability would allow the user 16 to focus the light rays reflected by the reflective surface areas 22 toward specific targeted areas of the user's 16 shoulders 18. It should be noted that the above regarding the wing members 36 and 38 and their adjustability is only given as an example and should not be seen as to limit the scope of the present invention.

The tanning device 10 may have a support area 30 formed in the main body 42. The support area 30 may be formed of a U-shaped groove area 20 formed in the main body 42. A section of the body 26 of the user 16 may be positioned in the groove area 20 of the support area 30. In accordance with one embodiment, the tanning device 10 may be placed under the head 12 (shown in FIGS. 4 and 6) of the user 16 (shown in FIGS. 4 and 6) during use, with the head 12 resting in, and being supported by, the groove area 20 of the support area 30, which may be located on the main body 42 between the wing members 36 and 38. However, it should be understood that an alternative embodiment of the tanning device 10 may have a support area 30 that may be differently located on the tanning device 10. It should also be understood that the support area 30 may support a portion of the user 16 in the absence of a groove area 20. Additionally, the groove area 20 may be differently shaped or may be used to support a portion of the user 16 other than the head 12 of the user 16. Furthermore, the tanning device 10 may have different or additional parts for supporting different parts of the body 26 of the user 16, such as a user's arms or feet. Further still, the tanning device 10 may be placed in a different area in proximity to the body 26 of the user 16 (shown in FIGS. 4 and 6), such as between a user's 16 knees or between a user's arms and body 26. It should be noted that the above is only given as an example and should not be seen as to limit the scope of the present invention.

The main body 42 of the tanning device 10 may also have a pair of inner parts 32 and 34 between the support area 30 and the wing members 36 and 38. In the present embodiment, the tanning device 10 may be shaped as depicted in the accompanying drawings, wherein the inner parts 32 and 34 and the wing members 36 and 38 are taller than the support area 30. However, an alternative embodiment of the tanning device 10 may have less parts, additional parts, or different parts, or may have inner parts 32 and 34 and wing members 36 and 38 that are differently shaped, positioned, or oriented. It should be noted that the above is only given as an example and should not be seen as to limit the scope of the present invention.

The tanning device 10 may have reflective surface areas 22 coupled to a portion of the outer surfaces of the inner parts 32 and 34 of the main body 42 and the wing members 36 and 38. Additional reflective surface areas 22 may be coupled to different or additional parts of the tanning device 10 without departing from the spirit and scope of the present invention. These reflective surface areas 22 may be adhered to their respective parts with a type of glue or some other adhesive, although it should be understood that the tanning device 10 may have reflective surface areas 22 that are incorporated with the tanning device 10 in some other manner without departing from the scope and spirit of the present invention. The reflective surface areas 22 may be made of mirror PLEXIGLAS, a reflective metal, acrylic mirror, and like material. The reflective surface areas 22 may redirect rays of light to the user's 16 shoulders 18 (shown in FIGS. 4 and 6).

In accordance with one embodiment, the reflective surface areas 22 coupled to the inner parts 32 and 34 may redirect rays of light to the tops of the user's shoulders 18, while the reflective surface areas 22 coupled to the wing members 36 and 38 may redirect rays of light to the sides of the user's 16 shoulders 18. However, it should be understood that an alternative embodiment of the tanning device 10 may redirect rays of light toward additional parts of the body 26 of the user 16, or toward other areas of the body 26 of the user 16, such as the user's underarms. It should be noted that the above references to the composition of the reflective surface areas 22 and the method in which they are integrated into the tanning device 10 are only given as an example and should not be seen as to limit the scope of the present invention.

The tanning device 10 may also have a plurality of rounded bumps 28 (shown in FIGS. 2 and 5) disposed about a bottom surface 24 of the tanning device 10. The rounded bumps 28 may have the ability to act as a gripping mechanism to aid in keeping the device 10 from moving during use. The bumps 28 of the tanning device 10 may be composed of either the same material or a different material as the rest of the tanning device 10. Furthermore, the bumps 28 of the tanning device 10 may be differently shaped or oriented, or may even be wholly absent. It should be noted that the reference to the rounded bumps 28 is only given as an example and should not be seen as to limit the scope of the present invention.

The tanning device 10 may also have a pair of speakers 50. The speakers 50 may be used to allow one to listen to audio files while using the tanning device 10. The speakers 50 may be positioned within the pair of inner parts 32 and 34 and or within the wing members 36 and 38. Thus, the pair of inner parts 32 and 34 and or the wing members 36 and 38 may have a void area for housing the speakers 50. The speakers 50 may be positioned behind the reflective surface areas 22. Alternatively, an opening 52 may be formed through the reflective surface areas 22 and a cover material 54 may be paced over the opening 52.

The speakers 50 may be coupled to a connector 56. The connector 56 may be a connector jack or the like. The connector 56 may allow one to attach an MP3 player, Ipod, or other like electronic devices to the speakers 50. Thus, one may be able to listen to desired audio files while using the tanning device 10.

This disclosure provides exemplary embodiments of the present invention. The scope of the present invention is not limited by these exemplary embodiments. Numerous variations, whether explicitly provided for by the specification or implied by the specification, such as variations in structure, dimension, type of material and manufacturing process may be implemented by one of skill in the art in view of this disclosure.

What is claimed is:

1. A light reflector for tanning comprising:
a main section having a planer bottom surface comprising:
  a support area;
  a single "U" shaped groove formed in a central area of the support area, wherein an opening of the "U" shaped groove extends across a width of the support area, the "U" shaped groove is dimensioned for positioning and supporting the desired portion of the body of the user within the "U" shaped groove;
  angled members extending from the support area up and away from the groove;
side members attached to the angled members of the main section, wherein the side members are adjustable to focus light rays towards a specific target area; and
a reflective coating formed on the angled members and the side members to reflect light to a desired location on the body of the user; and
a pair of speakers positioned within the angled members.

2. A light reflector for tanning in accordance with claim 1 further comprising a connector coupled to the pair of speakers for coupling an electronic device to the pair of speakers.

3. A light reflector for tanning in accordance with claim 1 further comprising a cover attached to the pair of speakers.

4. A light reflector for tanning in accordance with claim 1 further comprising bumps formed on a bottom surface of one of the main section or the side members to provide resistance to prevent the light reflector from moving during use.

5. A light reflector for tanning in accordance with claim 1 wherein the main section and the angled members of the main section are formed of a single foam unit.

6. A light reflector for tanning in accordance with claim 1 further comprising bumps formed on bottom surfaces of the main section and the side members to prevent the light reflector from moving during use.

* * * * *